United States Patent [19]
Kobayashi et al.

[11] 3,969,189
[45] *July 13, 1976

[54] CELL WALL-LYSING COMPLEX ENZYMES AND A PROCESS FOR THE PRODUCTION THEREOF

[75] Inventors: Reisuke Kobayashi, Shizuoka; Hironari Sato; Kiyoshi Takita, both of Shimizu; Nobuo Toyama, Miyazaki, all of Japan

[73] Assignee: Kumiai Chemical Industry Co., Ltd., Tokyo, Japan

[ * ] Notice: The portion of the term of this patent subsequent to June 17, 1992, has been disclaimed.

[22] Filed: Nov. 8, 1974

[21] Appl. No.: 522,304

Related U.S. Application Data

[63] Continuation of Ser. No. 314,933, Dec. 14, 1972, Pat. No. 3,890,198.

[30] Foreign Application Priority Data

Dec. 14, 1971  Japan.............................. 46-100700
Jan. 27, 1972  Japan................................. 47-9486

[52] U.S. Cl............................... 195/62; 195/66 R; 426/51

[51] Int. Cl.$^2$.................. C07G 7/028; C12D 13/10
[58] Field of Search.................. 195/62, 65, 66 R, 2; 426/51, 52

[56] References Cited
UNITED STATES PATENTS

| | | | |
|---|---|---|---|
| 3,658,650 | 4/1972 | Okazaki et al.................... | 195/66 X |
| 3,682,778 | 8/1972 | Kawai et al....................... | 195/62 X |
| 3,716,452 | 2/1973 | Kitamura et al..................... | 195/65 |

OTHER PUBLICATIONS

Bateman et al., Chemical Abstracts 71, 46787f (1969).
Geypens, Chemical Abstracts 77, 2581d (1972).

*Primary Examiner*—Lionel M. Shapiro
*Attorney, Agent, or Firm*—James C. Haight

[57] ABSTRACT

Complex enzymes which can lyse the cell wall of a variety of microorganisms such as bacteria, fungi, yeast, Basidiomycetes and chlorella are produced and recovered from cultivation of *Pellicularia sasakii* or *Pellicularia filamentosa*.

10 Claims, No Drawings

CELL WALL-LYSING COMPLEX ENZYMES AND A PROCESS FOR THE PRODUCTION THEREOF

This is a continuation of application Ser. No. 314,933, filed Dec. 14, 1972, now U.S. Pat. No. 3,890,198.

BACKGROUND OF THE INVENTION

This invention relates to novel complex enzymes which lyse, that is, disintegrate and dissolve the cell wall of various microorganisms, and this invention further relates to a process for the production of such complex enzymes.

It is known that yeasts and Chlorella etc., are cultured on large scale to utilise the cultured microorganisms in foodstuffs and feeds, and also that bacteria and fungi are cultured to use the cultured microorganisms for the recovery of useful substances such as antibiotics, protein, nucleic acid, amino acids, vitamins and enzymes from the culture. However, the cell wall of yeasts and Chlorella are so strong that their digestibility is poor in the use as foodstuff and feed. Accordingly it has been proposed to treat the yeasts and Chlorella with such an enzyme which digests the cell wall of these microorganisms, in order to improve their digestibility. Moreover, it has been proposed to treat the culture of bacteria or fungi with a cell wall-lysing enzyme in order to facilitate the extraction of useful intracellular substances from the cultured microorganisms.

SUMMARY OF THE INVENTION

We, the present inventors, have made extensive research to seek for such enzymes which are capable of lysing the cell and particularly the cell wall of various microorganisms. As a result, we have now found that complex enzymes which are produced by known strains of the genus Pellicularia exhibit a high ability to lyse, that is, dissolve the cells of various microorganisms, and that these complex enzymes can be obtained by cultivating the known strains of the genus Pellicularia in a culture medium containing assimilable carbon sources and assimilable nitrogen sources to produce and accumulate in the medium, and then isolating these complex enzymes from the medium.

According to a generic aspect of the present invention, therefore, there is provided a process for the production of a cell wall-lysing complex enzyme, which comprises cultivating a known strain of the genus Pellicularia in a culture medium containing assimilable carbon sources and assimilable nitrogen sources to produce and accumulate the complex enzyme in the medium, and then isolating the complex enzyme from the medium.

DETAILED DISCUSSION

According to the taxonomy, the genus Pellicularia falls within the family Corticiaceal of the order Aphyllophorales belonging to the subclass Homolasidine of the class Basidomycetes. As known examples of the known strains of the genus Pellicularia which may be used according to the present invention for the production of the cell wall-lysing complex enzyme, there may be mentioned the known species *Pellicularia sasakii* which is known to cause a plant disease "sheath blight" in rice plant; and the known species *Pellicularia filamentosa* which is known to cause a plant disease "black scurf" in potato plant. There are known some strains of *Pellicularia filamentosa* deposited under ATCC Nos. 14701, 14702, 14703 and 20206 and a strain of *Pellicularia sasakii* deposited under ATCC No. 13289 as shown on page 120 of the "Catalogue of strains" 9th Edition (in 1970) of the American Type Culture Collection.

We isolated a strain of *Pellicularia sasakii* from a lesion of the sheath blight infection in rice plant and deposited this strain under F.R.I. No. 1170 in a Japanese public depository "Fermentation Research Institute", Agency of Industrial Science & Technology of Japan, Inage, Chiba City, Japan on 8th Nov., 1971.

This strain was deposited unrestricted with the American Type Culture Collection, Rockville, Md., on Dec. 12, 1972, and has been designated ATCC No. 20,365. We also isolated a strain of *Pellicularis filamentosa* from a lesion of the black scurf infection in potato plant and deposited this strain under F.R.I. No. 1171 on the same date. This strain was deposited unrestricted with the American Type Culture Collection, Rockville, Md. on Dec. 12, 1972, and has been designated ATCC No. 20,366. Nevertheless, we are not able to differentiate the strains F.R.I. Nos. 1170 and 1171 from the known strains of *Pellicularia sasakii* and *Pellicularia filamentosa*, respectively, in view of the disclosure in a Japanese publication "Microbiology Handbook" pages 376–377 (published on 25th Dec., 1957 in Tokyo).

Morphological properties common to the abovementioned strains of *Pellicularia sasakii* and *Pellicularia filamentosa* are briefly described below.

i. The vegetable mycelium is in fibrous form or pileus-shaped and initially colorless and turning into yellowish brown color upon aging.

ii. The mycelium is generally of a diameter of 8–12 microns.

iii. The sclerotium is formed.

iv. The basidium is in the shape of barrel or obovoid and bears 4 or 8 branches.

v. Colorless spores of smooth surface are produced.

vi. The hymenium is flat.

vii. The fruit body forms a reticulated membrane.

The species *Pellicularia sasakii* and *Pellicularia filamentosa* may be differentiated from each other in that *Pellicularia sasakii* is causative of the sheath blight disease in rice plant; and *Pellicularia filamentosa* is causative of the black scurf disease in potato plant and damping-off disease in egg plant, and also in that *P. sasakii* forms blackish brown colored sclerotium of 5–13 mm, basidium measuring 18 × 9 microns and spore measuring 9 × 7 microns; and *P. filamentosa* forms brown colored sclerotium of 1–3 mm, basidium measuring 15 × 8 microns and spore measuring 9 ×7 microns. However, some taxonomers have stated that *Pellicularia sasakii* is merely a natural variant of the species *Pellicularia filamentosa*.

Any of the above-mentioned strains of *P. sasakii* and *P. filamentosa* may be used according to the present invention to produce the cell wall-lysing complex enzyme. According to an embodiment of the present invention, therefore, there is provided a process for the production of a cell wall-lysing complex enqyme, which comprises cultivating a known strain of *Fellicularia sasakii* or *Pellicularia filamentosa* in a culture medium containing assimilable carbon sources and assimilable nitrogen sources to produce and accumulate the complex enzyme in the medium, and then isolating the enzyme complex from the medium.

In carrying out the process of the present invention, a strain of the genus *Pellicularia*, particularly *Pellicularia sasakii* or *Pellicularia filamentosa* may be cultivated either in a liguid culture medium or in a solid culture medium using known fermentation technique. It is generally suitable to effect the cultivation of the Pellicularia strain at an incubation temperature of 15°–40°C for a period of 48 – 240 hours, though the cultivation conditions may vary depending on the manner of cultivation employed.

The culture medium in which the Pellicularia strain is cultivated according to the process of the present invention should contain assimilable carbon sources and nitrogen sources. Suitable examples of the carbon sources used are carbohydrates such as starch, glucose, sucrose, wheat bran, rice bran and the like. Suitable examples of the nitrogen sources are ammonium salts, nitrates, peptone, meat extract, yeast extract and defatted soybean meal, etc. It is feasible to incorporate a suitable amount of a growth-promoting substance such as vitamins into the culture medium employed. It is also possible to add a pulver of dried yeast, Chlorella and/or mushroom etc., to promote the production of the enzymes. Furthermore, traces of inorganic salts such as potassium salts, calcium salts, magnesium salts, iron salts, phosphates etc. may be incorporated into the culture medium to supply various trace elements which are essential to the growth of the Pellicularia strain.

The cultivation of the Pellicularia strain may proceed until a sufficient amount of the complex enzyme desired have been produced and accumulated in the culture medium. It is preferred to carry out the cultivation of the Pellicularia strain under aerobic conditions. In liquid cultivation, it is preferable that the cultivation should be conducted at 20° – 35°C for a period of 48 – 120 hours under aerobic, submerged conditions. In solid cultivation, it is suitable that the cultivation is conducted at 20° – 35°C for 3 to 10 days.

The complex enzyme which is lytic to the cell of verious micooganisms is produced and accumulated in the culture medium during the cultivation of the Pellicularia strain according to the present invention. A supernate of the culture broth which is obtained by filtering off or centrifuging the solid matters such as mycelium and solid residue of the culture medium therefrom may be used as such, for lysing the cell of various microorganisms. Such a supernate may also be freeze-dried to give a crude enzyme preparation. When the solid cultivation has been conducted, the resulting solid culture may be extracted with water or buffered water of pH 4.0 – 7.0 to give an aqueous extract containing the complex enzyme, which may be utilized similarly to the above-mentioned filtrate.

In order to isolate the complex enzyme in the form of a more purified enzyme preparation, the culture medium containing the enzymes may be freed from the solid matter, for example, by filtration or centrifugation, or it may be extracted with water or buffered water. The resulting aqueous crude solution of the complex enzyme may then be subjected to a treatment with a known salting-out agent such as ammonium sulfate, sodium chloide etc., or with a wate-miscible organic solvent such as lower aliphatic alcohols, for example, methyl or ethyl alcohol or acetone to precipitate the complex enzyme from the crude solution. For further purification, the precipitated complex enzyme may be dissolved in an appropriate buffer solution such as 0.01 M acetate buffered water and the enzyme solution may subsequently be subjected to a dialysis or gel-filtation process. The purified enzyme solution so obtained may then be freeze-dried to give the purified enzyme preparation essentially consisting of the desired complex enzyme.

The complex enzyme produced by *Pellicularia sasakii* and the complex enzyme produced by *Pellicularia filamentosa* according to the process of the present invention are soluble in water but insoluble in acetone and ethanol, and they have the following common characteristics:

a. being active to lyse the living cells and dead cells of bacteria, fungi, yeasts, Basidiomycetes and Chlorella, b. their cell wall-lysing activities being stable in a pH range of 3 – 9, the optimum pH being in the range of 5 – 7, c. being optimally active (cell wall-lysing activity) in a temperature range of 30° – 40°C, but the optimum temperature slightly varying depending on the nature of microorganisms of which cells are to be lysed, d. their cell wall-lysing activities being stable in a low temperature range but rapidly inactivated at a temperature of higher than 50°C, e. their cell wall-lysing activities being inhibited by the presence of $Mn^{++}$, $Ni^{++}$ or $Zn^{++}$, f. exhibiting the enzymatic activities of cellulase, glucanase, chitinase, protease, hemi-cellulase and carboxymethyl cellulase and g. being essentially composed of the component enzymes each having the molecular weights of at least 50,000.

It is considered that the cell wall-lysing complex enzyme produced by *Pellicularia sasakii* and the complex enzyme produced by *Pellicularia filamentosa* are each a mixture of cellulase, glucanase, chitinase, protease, hemi-cellulase and carboxymethyl cellulase in the form of a complex and exhibit their high activity of lysing the cell of various microorganisms through the synergistic effect of the actions of the particular component enzymes, though it is presumed that these complex enzymes produced by the different species of Pellicularia have compositions which are more or less different from each other, as it is observed that these complex enzymes show more or less different properties and potencies for the particular enzymatic activities.

According to a further aspect of the present invention, therefore, there is provided a cell wall-lysing complex enzyme selected from the complex enzyme produced by a known strain of *Pellicularia sasakii* and the complex enzyme produced by a known strain of *Pellicularia filamentosa*, all these complex enzymes having the following common characteristics:

a. being active to lyse the living cells and dead cells of at least Aspergillus niger, Penicillium steckii, Saccharomyces cerevvisiae, Candida utilis, Candida albicans, Candida lipolitica, Lentinus edodes, Bacillus subtilis, Lactobacillus lactic, and Chlorella, b. their cell wall-lysing activities being stable in a pH range of 3 to 9, the optimum pH being in the range of 5 to 7, c. their cell wall-lysing activities being optimal in a temperature range of 30° to 40°C, but the optimum temperature varying depending on the nature of microorganisms of which cells are to be lysed, d. their cell wall-lysing activities being stable in a low temperature range but rapidly inactivated at a temperature of higher than 50°C, e. their cell wall-lysing activities being inhibited by the present of $Mn^{++}$, $Ni^{++}$ or $Zn^{++}$, f. exhibiting the enzymatic activities of cellulase, carboxymethyl cellulase, glucanase, chitinase, protease, hemi-cellulase and amylase, and g. being essentially composed of the component enzymes each having the molecular weights of at least 50,000. The complex enzyme produced by *Pellicularia sasakii* further exhibits such a cellulase activity which has an optimum temperature range of 40° to 50°C and an optimum pH of 5.0, such a β-1,3-glucanase activity which has an optimum temperature range of 40° to 50°C an optimum pH of 5.0, and such a chitinase activity which has an optimum temperature of 35°C and an optimum pH range of 4.0 to 5.5. The complex enzyme produced by *Pellicularia filamentosa* further exhibits such a cellulase activity which has an optimum temperature range of 40° to 50°C and an optimum pH of 5.0, such a β-1,3-glucanase activity which has an optimum temperature range of 40° to 50°C and an optimum pH of 5.0, and such a chitinase activity which has an optimum temperature of 35°C and an optimum pH range of 4.0 to 5.5.

The cell wall-lysing activities referred to in the above-mentioned common characteristics (b) – (e) of the complex enzymes of the present invention are determined by the following procedure and scale: An amount of a complex enzyme preparation obtained is reacted with 5 ml of a suspension of the cells of *Candida utilis* IFO-0396 which shows an initial turbidity corresponding to an optical density (O.D.) value of 1.0 as measured at a wave length of 660 milimicrons. The reaction is effected at 35°C for 60 minutes at pH 5.0. After this reaction, the optical density of the cell suspension containing the lysed cells and unlysed cells is measured at 660 milimicrons. When the reacted cell suspension exhibits a reduction of 1% in the turbidity (or the O.D. value) as compared to the initial cell suspension, it is assumed that said amount of the complex enzyme preparation has a potency of 1 unit for the cell wall-lysing activity. Moreover, the cellulase activity, β-1,3-glucanase activity and chitinase activity referred to in the above of the complex enzymes of the present invention are measured in such manners as described later in Example 13 of this specification.

When the lysis, namely dissolution of the cell wall of a microorganism is effected using the complex enzyme of the present invention, the complex enzyme is reacted with the microorganism cells suspended in water. The reaction may suitably be carried out at a temperature of 20° – 60°C and preferably of 30° – 40°C at a pH of 2 – 10 and preferably at a pH of 3.4 – 8.0. The reaction temperature and pH value employed may be choosen appropriately depending on the nature of the microorganism of which cells are to be lysed under the action of the complex ensyme. The microorganism cells to be lysed may either be living or dead when they are brought into contact with the enzyme. In either case, substantially all the cells can be dissolved owing to the lysing of the cell wall and the contents (intracellular substances) of the cells can be released into the aqueous phase of the cell suspensions in 20 hours after the start of the reaction.

In order to carry out the reaction of the complex enzyme with the microorganism cells, either the enzyme preparation in the form of a solid powder or an aqueous solution thereof or the culture broth or an extract of the culture may be needed to a suspension of the cells in water which has been buffered to a pH value optimal to effect the enzymatic reaction. Alternatively, the cells may be added to a solution of the enzyme preparation in water or in a buffer solution which has been adjusted to a pH value optimal to effect the enzymatic reaction. When the reaction has been effected to completion, the cells have wholly been dissolved without leaving any solid residue in the solution. In some cases, however, an amount of a solid residue remains even after the reaction was completed. Whether the cells have been dissolved to a desired degree, it can be estimated by determining the variation in the turbidity of the cell suspension or the concentration of a soluble component of the cell protoplasm, or by observing microscopically the conditions of the cells in the suspension. In this way, there may be obtained an aqueous cell solution in which the material of the cell membranes and the protoplasm of the cells have been dissolved in water together with the complex enzyme employed. If desired, the cell solution so obtained may be filtered to remove any possible solid residue. This solution may also be heated to deactivate the remaining enzymes, if necessary. The cell solution so obtained may subsequently be processed merely be dehydration or concentration in vacuo to give a dry product. The cell solution may also be treated by a suitable means such as extraction or chromatography, to recover any useful substance or substances therefrom.

The complex enzyme of the present invention are able to lyse the cells (exactly speaking, the cell wall) of various microorganisms such as bacteria, fungi, yeast, Besidiomycetes as well as chlorella, one of algae. This property of the complex enzyme according to the present invention is more advantageous and useful, as compared to e.g. the known enzyme which is isolated from the culture of *Corticium rolfsii* according to the method of Japanese patent publication No. 11978/67. The enzyme as isolated from the culture of *Corticium rolfsii* has an optimum pH range of 2.0 – 2.5 and a limited ability that they can lyse the cell wall of yeast and chlorella only. The microorganisms of the genus Corticium can be differentiated from those of the genus Pellicularia in that the former produces such a continuous hymenium wherein the basidium are arranged side by side in a continuous manner, while the latter produces such a discontinuous hymenium wherein the basidium are spaced from each other.

According to an another aspect of the present invention, therefore, there is provided a method of dissolving the cells of microorganisms, including bacteria, fungi, yeasts, Basidiomycetes and chlorella, which comprises treating the cells suspended in an aqueous medium, with the cell wall-lysing complex enzyme which is by a known strain of *Pellicularia sasakii* or *Pellicularia filamentosa* or with a culture broth of said strain or an extract thereof.

The cell wall-lysing complex enzyme of the present invention may be applied in the extraction of useful intracellular substances from the cells as well as in the production of a concentrated extract comprising nutrient substances or other useful substances present in the protoplasm in the cells of various microorganisms such as yeasts, chlorella, bacteria and fungi. For these purposes the cells are treated with the complex enzyme in water to lyse the cell wall and to release the protoplasm so as to give a cell solution which may then be dehydrated partially or completely to give a concentrate or a dry powder. Furthermore, the cell wall-lysing complex enzyme of the present invention may be applied for the purpose of preventing foodstuff or drinks from spoiling, by incorporating an effective amount of the complex enzyme therein and allowing to dissolve the cells of bacteria or fungi which would possibly occur or be present in the foodstuff or drinks and to which the spoiling of the foodstuffs or drinks is attributable. Thus, the complex enzymes of the present invention find wide applications in many fields such as the food industry, pharmaceutical industry, pesticide industry and feed-preparing industry.

The present invention is now illustrated with reference to the following Examples to which the invention is not limited in any way.

EXAMPLE 1

In a conical flask of a 300 ml. capacity were placed 19 g. of wheat bran, 1 g. of dried yeast and 18 ml. of water. The flask was then warmed and the content of the flask was agitated to give a uniform pasty mixture. This culture medium was steamed at 120°C for 20 minutes for sterilization. A stock culture of *Pellicularia sasakii* (F.R.I. No. 1170) was inoculated to the sterile culture medium. Solid cultivation of the Pellicularia strain was carried out for 120 hours at a constant temperature of 28°C. The resulting culture was mixed with 80 ml. of an acetate buffer solution, pH 4.0, and the mixture was agitated at ambient temperature for 1 hour to ensure that the enzyme were extracted into the liquid phase. The mixture was then filtered under pressure and the filtrate obtained was centrifuged to give 70 ml. of a clear solution containing the complex enzyme which was produced by *Pellicularia sasakii*. To this clear solution was added 210 ml. of acetone, so that the complex enzyme was precipitated. The precipitate was filtered out and dried to give 700 mg. of an enzyme preparation in the powder form. This enzyme preparation was found to be active to lyse the cell wall of a variety of microorganisms, including bacteria, fungi, yeasts, Basidiomycetes and chlorella.

EXAMPLE 2

In a 300 ml. conical flask were placed 10 g. of wheat bran, 10 g. of rice bran, 2 g. of peptone and 20 ml. of water. The flask was warmed and the content of the flask was agitated to give a uniform pasty mixture. This culture medium was steamed at 120°C for 20 minutes for sterilization. A stock culture of *Pellicularia filamentosa* (F.R.I. No. 1172) was inoculated to the sterile culture medium. Solid cultivation of the Pellicularia strain was carried out at 28°C for 170 hours. The culture so obtained was then mixed with 80 ml. of water and the mixture was well agitated at ambient temperature to ensure that the enzymes were extracted into the aqueous phase. The mixture was filtered under pressure and the filtrate obtained was centrifuged to give a clear solution containing the complex enzyme which was produced by *Pellicularia filamentosa*. To the clear solution was added ammonium sulfate to a 70% saturation, so that the complex enzyme was precipitated. The precipitate was filtered out and dried to give 1 g. of a enzyme preparation in the powder form. This enzyme preparation was found to be active to lyse the cell wall of a variety of microorganisms, including bacteria, fungi, yeasts, Basidiomycetes and chlorella.

EXAMPLE 3

In an 1-liter conical flask were placed 9 g. of sucrose, 6 g. of rice bran, 0.6 g. of a powder of dried mushroom (*Cortinellus shiitake*), 1.5 g. of ammonium sulfate, 1.5 g. of mono-potassium phosphate, 0.3 g. of potassium chloride, 0.3 g. of magnesium sulfate and 0.003 g. of ferrous sulfate. To the content of the flask was added 300 ml. of water to effect the dissolution of the soluble matter. The culture medium in the form of an aqueous solution was sterilized by steaming at 120°C for 20 minutes. A stock culture of *Pellicularia filamentosa* (F.R.I. 1172) was inoculated to the sterile liquid culture medium. Shake-cultivation of the Pellicularia strain was carried out at 25°C for 120 hours. The culture broth so obtained was filtrated to remove the solid matter present, and the resulting clear filtrate containing the enzyme was concentrated to a volume of one-third the original volume, by dialysing through a dyalisis membrane. To the concentrated solution was added 400 ml. of aqueous 99% ethyl alcohol, so that the complex enzyme was precipitated. The precipitate was filtered and dried to give 450 mg of an enzyme preparation in the powder form. This enzyme preparation was found to be active to lyse the cell wall of a variety of microorganisms, including bacteria, fungi, yeasts, Basidiomycetes and chlorella.

EXAMPLE 4

In a 300 ml. conical flask were placed 5 g. of finely divided wheat bran, 0.5 g. of ammonium sulfate, 0.5 g. of mono-potassium phosphate, 0.1 g. of potassium chloride, 0.1 g. of magnesium sulfate, 0.001 g. of ferrous sulfate and 100 ml. of water. The content of the flask was sterilized by steaming at 120°C for 20 minutes. A stock culture of *Pellicularia sasakii* (F.R.I. No. 1170) was inoculated to the sterile liquid culture medium. Shake-incubation was carried out at 28°C for 24 hours by means of a rotary shaker to prepare a liquid seed culture. On the other hand, 200 g. of wheat bran, 5 g. of a powder of dried mushroom (*Cortinellus shiitake*) and 160 ml. of an aqueous solution of 5% ammonium sulfate were placed in 5 wooden trays, respectively. In each tray, the materials were well mixed with each other to give a uniform mixture which was then sterilized by steaming. 20 ml. of the abovementioned liquid seed culture prepared was inoculated to the culture medium in each tray. Stationary cultivation was conducted at 28° C for 96 hours. The cultures in these trays were combined together, and the combined culture was extracted with 4 l. of an aqueous solution of acetate buffer pH 4.0. The extract was filtered under pressure and the filtrate was centrifuged to give 3.6 l. of a clear solution containing the complex enzyme which was produced by *Pellicularia sasakii*. To this clear solution was added ammonium sulfate to 70% saturation, so that the complex enzyme was precipitated. The precipitate was collected and taken up in 900 ml. of water. The aqueous enzyme solution was lyophillized in vacuo to give 32 g. of an enzyme preparation in the form of a powder. This enzyme preparation was found to be active to lyse the cell wall of a variety of microorganisms, including bacteria, fungi, yeasts, Basidiomycetes and chlorella.

EXAMPLE 5

In each of three conical flasks of a 300 ml. capacity were placed 19 g. of wheat bran, 1 g. of dried yeast and 18 ml. of water, and the contents of each flask warmed and agitated to give a uniform pasty mixture. This culture medium was sterilized by steaming at 120°C for 20 minutes. Stock cultures of *Pellicularia sasakii* and *Pellicularia filamentosa* were inoculated to the sterile culture media in these flasks, respectively. Solid cultivation was made for 120 hours at a constant temperature of 28°C. After this cultivation, the cultures obtained were mixed with 80 ml. portions of an acetate buffer solution and the mixtures were agitated at ambient temperature for 1 hour to ensure that the complex enzymes produced by the different species of Pellicularia were extracted into the liquid phases. The mixtures were filtered under pressure and the filtrates obtained were centrifuged to give 70 ml. portions of two clear solutions containing the complex enzymes, respectively.

On the other hand, cell suspensions of fungi, yeasts, bacteria and chlorella in water was prepared from cultures of *Aspergillus niger*, *Penicillium steckii*, *Saccharomyces cerevisiae* IFO-0209, *Candida utilis* IFO-0396, *Candida albicans*, *Candida lipolitica* and *Lentinus edodes* each incubated in malt media; cultures of *Bacillus subtilis* and *Lactobacillus lactis* each incubated bouillon media; and culture of *Chlorella pyrenoidosa* incubated in Nakamura medium, respectively. Each of these cell suspensions so prepared was placed in three test tubes. 20 ml. portions of the above-mentioned three clear solutions of the complex enzyme were then added to the three test tubes each containing the cell suspensions, respectively. The content in each test tube was gently shaken for 20 hours in a water bath at a constant temperature of 35°C., so that the enzymes were reacted with the cell wall to dissolve the cells in the suspension. The cell suspensions were observed under microscope to estimate how much is the degree to which the cells had been dissolved or digested under the action of the complex enzymes of *Pellicularia sasakii* and *Pellicularia filamentosa*.

The degree of dissolution of the cells was estimated on the following scale:

The symbol ++ denotes that there was observed the dissolution of all the cells.

The symbol + denotes that there was observed the dissolution of a larger part of the cells.

The symbol ± denotes that there was observed the dissolution of a minor part of the cells.

The symbol − denotes that there was not observed any dissolution of the cells.

The test results obtained are shown in Table 1 below. For comparison, the test procedure was repeated adding 2 ml. of the acetate buffer solution at instead of the above-mentioned clear enzyme solutions. In the comparative tests, no dissolution of the cells was observed.

TABLE 1

| Nature of the cells to be dissolved | Addition of enzyme | Degree of dissolution of cells by | |
|---|---|---|---|
| | | Enzyme of Pellicularia sasakii | Enzyme of Pellicularia filamentose |
| Aspergillus niger | Added | ++ | ++ |
| | Not added | − | − |
| Penicillium steckii | Added | ++ | ++ |
| | Not added | − | − |
| Saccharomyces cerevisiae | Added | ++ | ++ |
| | Not added | − | − |
| Candida utilis | Added | ++ | ++ |
| | Not added | − | − |

TABLE 1-continued

| Nature of the cells to be dissolved | Addition of enzyme | Degree of dissolution of cells by | |
|---|---|---|---|
| | | Enzyme of Pellicularia sasakii | Enzyme of Pellicularia filamentose |
| Candida albicans | Added | ++ | ++ |
| | Not added | − | − |
| Candida lipolitica | Added | ++ | ++ |
| | Not added | − | − |
| Lentinus edodes | Added | + | + |
| | Not added | − | − |
| Bacillus subtilis | Added | ± | ± |
| | Not added | − | − |
| Lactobacillus lactis | Added | + | + |
| | Not added | − | − |
| Chlorella pyrenoidosa | Added | + | + |
| | Not added | − | − |

EXAMPLE 6

Cell suspensions in physiological saline water were prepared from cultures of *Candida utilis* IFO-0396, *Saccharomyces cerevisiae* IFO-0209 and *Hansenula anomala* IFO-0122 which were each obtained by shake-cultivating the microorganism in a liquid culture medium comprising 3% glucose, 0.8% $(NH_4)_2SO_4$, 0.5% $KH_2PO_4$, 0.2% NaCl, 0.2% $MgSO_4 \cdot 7H_2O$ and 0.1% yeast extract (by weight), pH 5.2, for a period of 20 hours while the shaking was made by means of a rotator (200 r.p.m.). One drop of each of the cell suspensions so prepared was placed on a slide glass plate, and one drop of the clear solution of the complex enzyme of *Pellicularia sasakii* given in Example 1 was added to the one drop of the cell suspension on the slide glass plate. The liquids of these drops were rapidly mixed together and then covered with a covering glass plate. The slide glass plate was placed in a room at a constant temperature of 30°C, and the change of the cells in the liquid mass on the glass plate was observed under microscope for a period of time. It was observed that the cells were gradually dissolved as the time lapsed. The degree of dissolution of the cells observed was estimated on the following scale:

The symbol + denotes that the dissolution of the cells took place.

The symbol ++ denotes that the dissolution of the cells were advancing.

The symbol +++ denotes that the dissolution of all the cells had been completed.

The symbol − denotes that no change in the cells was observed.

The test results obtained are shown in Table 2 below. For comparison, the test procedure was repeated adding one drop of the acetate buffer solution, instead of the one drop of the enzyme solution. In the comparative tests, no dissolution of the cells was observed.

TABLE 2

| Microorganism to be dissolved | Addition of enzyme | Degree of dissolution of the cells of the microorganisms with lapse of time (minutes) | | | | | | | |
|---|---|---|---|---|---|---|---|---|---|
| | | 1 | 3 | 5 | 10 | 15 | 30 | 60 | 90 |
| Candida utilis | Added | + | ++ | ++ | +++ | | | | |
| | Not added | − | − | − | − | − | − | − | − |
| Saccharomyces cerevisiae | Added | − | − | + | +++ | | | | |
| | Not added | − | − | − | − | − | − | − | − |
| Hansenula anomala | Added | − | − | − | − | + | ++ | ++ | +++ |
| | Not | − | − | − | − | − | − | − | − |

TABLE 2-continued

| Microorganism to be dissolved | Addition of enzyme added | Degree of dissolution of the cells of the microorganisms with lapse of time (minutes) |||||||
|---|---|---|---|---|---|---|---|---|
| | | 1 | 3 | 5 | 10 | 15 | 30 | 60 | 90 |

EXAMPLE 7

In a 300 ml. conical flask were placed 20 g. of wheat bran, 0.5 g. of a powder of dried mushroom (*Cortinellus shiitake*) and 16 ml. of an aqueous solution of 5% ammonium sulfate, and the contents of the flask warmed and agitated to give a uniform pasty mixture. This culture medium was sterilized by steaming at 120°C for 20 minutes. A stock culture of *Pellicularia filamentosa* was inoculated to the sterile culture medium, and solid cultivation thereof was conducted at 25°C for 144 hours. The culture obtained was mixed with 80 ml. of de-ionized water and the mixture was agitated at ambient temperature for 1 hour to ensure that the complex enzyme produced by *Pellicularia filamentosa* were extracted into the liquid layer. The mixture was filtered under pressure and the filtrate was centrifuged to give 65 ml. of a clear solution containing the complex enzyme. To this clear solution was added ammonium sulfate to 70% saturation, so that the complex enzyme was precipitated. The precipitate was filtered out and dried to yield 1.7 g. of an enzyme preparation in the form of a powder.

This enzyme preparation was dissolved in an acetate buffer solution, pH 5.0 to prepare an enzyme solution container 1% of said enzyme preparation. 10 ml. of this enzyme solution was placed in a bent tube in the shape of a letter L, and 1 g. of dried yeast (this yeast was a species of Candida which was incubated using a culture medium containing paraffinic hydrocarbon fraction of petroleum oil as the carbon sources) or 1 g. of dried chlorella was additionally placed into the L-shaped tube. The bent tube was shaken at a constant temperature of 40°C., so that the enzymes were reacted with the cells of yeast or chlorella to effect the lysis of the cell wall. After a reaction time of 1 hour or 3 hours, 3 ml. of aqueous sodium hydroxide was added to the reaction mixture within the bent tube to adjust the pH to about 7. The mixture was again shaken for further 15 minutes and then centrifuged to remove the solid matter therefrom. The clear solution obtained was analysed for the contents of sugars and proteins which were dissolved out of the cells. The quantity of the sugars was determined by a colorimetric method at 530 mu using 3,5-dinitro-salicyclic acid as the color-developing agent and was expressed in the term of the quantity of glucose. The quantity of the proteins was calculated by determining the nitrogen content in the proteins by the known Kjeldahl-ninhydrin method, and multiplying the determined nitrogen content by 6.25.

The test results obtained are shown in Table 3 below. For comparison, the test procedure was repeated adding 10 ml. of an acetate buffer solution, pH 5.0 in place of the above-mentioned enzyme solution.

TABLE 3

| Microorganism to be dissolved | Addition of enzyme | Reaction time (in hour) | Contents of the substances dissolved out of the cells (in mg.) ||
|---|---|---|---|---|
| | | | Sugars | Proteins |
| Dried yeast | Added | 1 | 70.2 | 291.0 |
| | | 3 | 75.4 | 368.2 |
| | Not added | 1 | 5.7 | 95.1 |
| | | 3 | 5.6 | 95.4 |
| Dried chlorella | Added | 1 | 30.3 | 162.2 |
| | | 3 | 34.1 | 198.9 |
| | Not added | 1 | 0.4 | 40.1 |
| | | 3 | 0.4 | 40.6 |

EXAMPLE 8

This example is to show that the complex enzyme of the present invention is useful to prevent various foodstuffs and drinks such as tomato juice, potato juice and orange juice from spoiling.

10 ml. Portions of tomato juice, potato juice or orange juice were placed in small dishes. On the other hand, the enzyme preparation produced in Example 1 was purified by means of an ion-exchange resin. 0.1 mg, 1 mg. and 10 mg. of the resulting purified enzyme preparation were added to the contents of the dishes, respectively. Some dishes containing the foodstuffs or drinks were not added with the enzyme preparation, as control. The dishes were maintained in air at 28°C for a period of time and then the occurrence of spoiling was checked by observing discoloration, appearance and odor of the juices. The test results are shown in Table 4 below. In this table, the symbol + denotes the spoiling occurred and the symbol − denotes no spoiling occurred.

TABLE 4

| Material | Addition of enzyme | Time lapse (days) ||||
|---|---|---|---|---|---|
| | | 1 | 2 | 4 | 7 |
| Tomato juice | Not added | − | + | + | + |
| | 0.1 mg/10 ml. | − | − | − | + |
| | 1 mg/10 ml. | − | − | − | − |
| | 10 mg/10 ml. | − | − | − | − |
| Potato juice | Not added | + | + | + | + |
| | 0.1 mg/10 ml. | − | − | + | + |
| | 1 mg/10 ml. | − | − | + | + |
| | 10 mg/10 ml. | − | − | − | − |
| Orange juice | Not added | − | − | + | + |
| | 0.1 mg/10 ml. | − | − | − | − |
| | 1 mg/10 ml. | − | − | − | − |
| | 10 mg/10 ml. | − | − | − | − |

EXAMPLE 9

To 100 g. of dried cell cake of a yeast *Candida lipolitica* was added 1 liter of an aqueous solution (pH 5.0) of 0.5% of the enzyme preparation which was produced in Example 2. The mixture was kept at 35°C for 30 minutes to effect the enzymatic reaction, and the reaction mixture was then added with 1 liter of aqueous 0.2 N sodium hydroxide. The mixture was heated at 50°C for 30 minutes to ensure that the protein of the yeast cells was extracted into the aqueous phase. The aqueous extract obtained was centrifuged to remove the cell cake, and the supernatant solution was adjusted to pH 4.0 by addition of 6N hydrochloric acid so that the protein was precipitated at the isoelectric point. The quantity of protein precipitated and recovered was corresponds to 76% of the whole protein content of the yeast cells. When the test procedure was repeated without the enzyme preparation, the quantity of the protein precipitated and recovered corresponded only to 15 % of the whole protein content of the yeast cells.

EXAMPLE 10

10 g. of a feed consisting of dried cells of *Candida utilis* was added to 100 ml. of an aqueous solution (pH 6.0) containing 0.5% of the enzyme preparation which was produced in Example 3. The mixture was kept at 35°C for 1 hour so that the enzymes reacted with the cell wall of the yeast. The reaction mixture was freeze-dried to give a powder feed consisting of the enzyme-treated Candida yeast. The procedure was repeated without the enzyme preparation, to give a powder feed consisting of the merely freeze-dried Candida yeast. The initial dried Candida yeast untreated, the enzyme-treated Candida yeast and the merely freeze-dried were treated with pepsine to estimate their digestibility. The results obtained are shown in Table 5 below.

TABLE 5

| Samples | Digestibility by pepsin |
|---|---|
| Dried Candida yeast untreated (comparative) | 58.4% |
| Merely freeze-dried Candida yeast (comparative) | 60.2% |
| Candida yeast treated with the complex enzyme of the present invention | 97.7% |

EXAMPLE 11

To a volume of a clear solution containing the complex enzyme of *Pellicularia sasakii* which was obtained in Example 5 was added a two-fold volume of acetone, so that the complex enzyme was precipitated. The precipitate was collected and dried to give a powdery enzyme preparation. 20 g. of a wet cake (solid content; 48% by weight) consisting of the cells of *Candida utilis* was added to 100 ml. of an aqueous solution (pH 4.0) containing 1% of said powdery enzyme preparation. The mixture obtained was gently shaken at 35°C for 1 hour to effect the enzymatic reaction. After the reaction, the reaction mixture was centrifuged to remove the remaining solid matter. The supernatant solution was lyophillized to give 7.8 g. of a dry powdery extract of the soluble, intracellular substances of the cells of *Candida utilis*. By analysis, this dry powdery extract was found to contain 54.3% crude proteins, 4.0% crude fats, 1.7% crude fibrous materials, 6.4% ashes and 33.6% soluble nitrogenous substances.

When the process was repeated adding 100 ml. of an acetate buffer solution, pH 4.0 instead of the enzyme solution, there was obtained only 1.7 g. of a dry powder after the lyophillisation of the supernatant solution.

EXAMPLE 12

An inoculant of *Candida albicans*, a pathogenic yeast, was prepared by inoculating a slant culture of this yeast to 100 ml. of potato-glucose medium, incubating at 30°C for 24 hours and then diluting the medium with water to a volume of 10 times the original volume thereof. One ml. portions of the inoculant so prepared (containing $6 \times 10^4$ cell colonies of yeast per ml.) were added to 10 ml. portions of a potato-glucose medium (pH 6.0) containing 0.5, 1, 2, 4, 8, 16 and 32 mg/ml. of the enzyme preparation of *Pellicularia sasakii* of Example 1, respectively. The inoculated media were incubated stationarily at 35°C for 24 hours, and thereafter the number of the unlysed cells of *Candida albicans* was counted. The results obtained are shown in Table 6 below.

TABLE 6

| Content of the enzyme preparation in the incubated media (mg./ml.) | Number of cell colonies per ml. of the media |
|---|---|
| None | $2 \times 10^6$ |
| 0.5 | $1 \times 10^5$ |
| 1 | $7 \times 10^4$ |
| 2 | $4 \times 10^4$ |
| 4 | $2 \times 10^2$ |
| 8 | 0 |
| 16 | 0 |
| 32 | 0 |

EXAMPLE 13

Enzymatic activities were determined of the complex enzymes which were produced from the cultures of *Pellicularia sasakii* and *Pellicularia filamentosa* by the processes of Examples 4 and 2, respectively. The determination of the enzymatic activities were conducted in the following manners:

i. Cellulase activity: 5 ml. of an enzyme solution in water was placed in an L-shaped tube, and two pieces of filter paper (measuring 1 cm by 1 cm.) were immersed in the enzyme solution within the tube. The solution was shaken at 40°C and the time taken until the filter paper pieces had been disintegrated completely was determined. Potency of the cellulase activity was calculated according to the following equation:

$$\text{Potency} = \frac{150}{(x)(y)} \times 1000$$

wherein $(x)$ denotes the time (in minutes) taken until the filter paper pieces had been disintegrated completely, and $(y)$ denotes the volume (in ml.) of the enzyme solution employed.

ii. $\beta$-1,3-Glucanase activity: 0.5 ml. of a solution of 1% of laminarin was placed in a test tube and then added with 0.5 ml. of a diluted enzyme solution (pH 5.0) and the mixture was heated at 40°C for 30 minutes. After this, the determination of the quantity of the glucose present in the reaction mixture was conducted colorimetrically. 1 mg. of glucose formed in the reaction mixture was taken as corresponding to 1 unit of the $\beta$-1,3-glucanase activity per 0.5 ml. of said diluted enzyme solution.

iii. Chitinase activity: This activity was measured using 1 ml. of a suspension of 1% of powdered (100 mesh) poly-N-acetylglucosamine, pH 5.0 and reacting therewith 1 ml. of a diluted enzyme solution at 40°C for 2 hours. Formation of 1 mcg./ml. of N-acetylglucosamine in the reaction mixture was taken as corresponding to 1 unit of the chitanase activity per ml. of said enzyme solution.

The optimal temperature and optimal pH for the respective enzyme activities were also measured for the enzyme preparations produced by *Pellicularia sasakii* and *Pellicularia filamentosa*. The results obtained are shown in Tables 7 and 8 below.

TABLE 7

Properties of the complex enzyme produced by P. sasakii

| Enzymatic activities | Potency (u./ml) | Optimal temperature (°C) | Optimal pH |
|---|---|---|---|
| Cell wall-lysing activity | 210 | 30 – 40 | 5 – 7 |
| Cellulase | 500 | 40 – 50 | 5.0 |
| β-1,3-Glucanase | 17.0 | 40 – 50 | 5.0 |
| Chitinase | 12.5 | 35 | 4.0–5.5 |

TABLE 8

Properties of the complex enzyme produced by P. filamentosa

| Enzymatic activities | Potency (u./ml.) | Optimal temperature (°C) | Optimal pH |
|---|---|---|---|
| Cell wall-lysing | 220 | 30 – 40 | 5 – 7 |
| Cellulase | 500 | 40 – 50 | 5 |
| β-1,3-Glucanase | 17.2 | 40 – 50 | 5.0 |
| Chitinase | 12.0 | 35 | 4.0–5.5 |

What we claim is:

1. A powdery complex enzyme isolated from Pellicularia culture media, capable of lysing cell walls and having the following characteristics:
   a. being active to lyse the cell walls of living cells and dead cells of *Aspergillus niger*, *Penicillium steckii*, *Saccaromyces cerevisiae*, *Candida utilis*, *Canadida albicans*, *Candida lipolitica*, *Lentinus edodes*, *Bacillus subtilis*, *Lactobacillus lactis* and *Chlorella*;
   b. having cell wall-lysing activities stable in a pH range of 3 to 9, the optimum pH being in the range of 5 to 7;
   c. said cell wall-lysing activities being optimal in a temperature range of 30° or 40°C., but the optimum temperature varying depending on the nature of the microorganisms of which cells are to be lysed;
   d. said cell wall-lysing activities being stable in a low temperature range but rapidly inactivated at a temperature of higher than 50°C.;
   e. said cell wall-lysing activities being inhibited by the presence of $Mn^{++}$, $Ni^{++}$ or $Zn^{++}$;
   f. exhibiting the enzymatic activities of cellulase and β-1,3-glucanase at an optimum temperature of 40°–50°C. and an optimum pH of 5.0, chitinase at an optimum temperature of about 35°C. and an optimum pH of 4.0–5.5, protease, hemicellulase and amylase; and
   g. consisting essentially of component enzymes each having a molecular weight of at least 50,000.

2. A complex enzyme according to claim 1, having a relative cell wall-lysing activity of about 210 units, a relative cellulase activity of about 500 units, a relative β-1,3-glucanase activity of about 17.0 units and a relative chitinase activity of about 12.5 units.

3. A complex enzyme according to claim 1, obtained from Pellicularia sasakii ATCC 20,365.

4. A complex enzyme according to claim 1, obtained from *Pellicularia filamentosa*.

5. A process for the production of a complex enzyme capable of lysing cell walls of microorganisms, which comprises cultivating a strain of the genus Pellicularia in a culture medium containing assimilable carbon sources and assimilable nitrogen sources to produce and accumulate the complex enzyme in the medium, and then isolating the complex enzyme from the medium.

6. A process as claimed in claim 5 in which liquid cultivation of *Pellicularia sasakii* or *Pellicularia filamentosa* is conducted at a temperature of 20°–35°C. for a period of 48–120 hours under aerobic conditions.

7. A process as claimed in claim 5 in which solid cultivation of *Pellicularia sasakii* or *Pellicularia filamentosa* is conducted at a temperature of 20°–35°C. for a period of 3 to 10 days under aerobic conditions.

8. A process as claimed in claim 5, which comprises cultivating *Pellicularia sasakii* or *Pellicularia filamentosa* in a culture medium containing bran as an assimilable nitrogen source to produce and accumulate the complex enzyme in the medium, extracting the medium with water or buffered water to give an aqueous extract solution of the complex enzyme, precipitating the complex enzyme from the extract and drying the resultant precipitate.

9. A process as claimed in claim 5, which comprises cultivating *Pellicularia sasakii* or *Pellicularia filamentosa* in a liquid culture medium containing assimilable nitrogen sources under aerobic conditions to produce and accumulate the complex enzyme in the liquid medium, filtering the resulting culture broth to remove solid matter, concentrating the clear filtrate obtained, precipitating the complex enzyme from the concentrated filtrate and drying the resultant precipitate.

10. A process according to claim 5, in which said Pellicularia strain is *Pellicularia filamentosa*.

* * * * *